(12) United States Patent
Al-Sabi et al.

(10) Patent No.: US 11,771,070 B1
(45) Date of Patent: Oct. 3, 2023

(54) IN VITRO FEEDING SYSTEM FOR GROWING OESTRIDAE LARVAE

(71) Applicant: KING FAISAL UNIVERSITY, Al-Ahsa (SA)

(72) Inventors: Mohammad Nafi Solaiman Al-Sabi, Al-Ahsa (SA); Ahmed Meligy Abdelghany Meligy, Al-Ahsa (SA); Abdullah Ibrahim Abdulaziz Al-Mubarak, Al-Ahsa (SA); Ahmad Mohammad Alnajjad, Al-Ahsa (SA); Abdullah Nasser Bu Qursayn, Al-Ahsa (SA); Saad Khalid Almuhaysin, Al-Ahsa (SA); Mahdi Mohammed Almatar, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/198,598

(22) Filed: May 17, 2023

(51) Int. Cl.
*A01K 67/033* (2006.01)

(52) U.S. Cl.
CPC .................. *A01K 67/033* (2013.01)

(58) Field of Classification Search
CPC .................................... A01K 67/033
USPC ......................................... 119/6.5
See application file for complete search history.

(56) References Cited

U.S. PATENT DOCUMENTS

| | | | | |
|---|---|---|---|---|
| 3,468,289 A | * | 9/1969 | Broida | B65D 81/266 119/6.5 |
| 4,417,545 A | * | 11/1983 | Finney | A01K 67/033 119/6.6 |
| 5,351,643 A | * | 10/1994 | Hughes | A01K 67/033 119/6.5 |
| 6,557,487 B1 | * | 5/2003 | Fleischmann | A61K 35/63 119/6.5 |
| 10,292,375 B1 | * | 5/2019 | Massaro | B01D 35/02 |
| 10,306,875 B1 | * | 6/2019 | Massaro | A01K 67/033 |
| 10,779,521 B2 | * | 9/2020 | Massaro | G06Q 50/02 |

FOREIGN PATENT DOCUMENTS

| | | |
|---|---|---|
| CN | 105052840 A | 11/2015 |
| CN | 206835969 A1 | 1/2018 |
| SU | 1607759 A1 | 11/1990 |

OTHER PUBLICATIONS

Perez et al., "In vitro feeding system for rearing oestridae larvae", Parasite vol. 13, No. 4, Dec. 2006.

* cited by examiner

*Primary Examiner* — Yvonne R Abbott-Lewis
(74) *Attorney, Agent, or Firm* — Nath, Goldberg & Meyer; Richard C. Litman

(57) ABSTRACT

A two-tier in vitro growth apparatus and method for cultivating Oestridae larvae and maggots is provided. The growth apparatus includes a top tier container and a bottom tier container where the top tier container has a growth container residing within the volume of the top tier container. The growth container is constructed of a semipermeable material and facilitates cultivating Oestridae larvae and maggots within an interior space of the growth container.

19 Claims, 3 Drawing Sheets

IN VITRO FEEDING SYSTEM FOR GROWING OESTRIDAE LARVAE

BACKGROUND

1. Field

The present invention relates to a method and system for cultivating larvae or maggots of the Oestridae family.

2. Description of the Related Art

The larvae and maggots of the Oestridae family (Bot Flies) are cultivated for a variety of endeavors in scientific research by pharmaceutical companies, life science companies, research laboratories, universities, institutional, and governmental bodies in order to combat Oestridae infections in animals. However, normal modes of cultivation of Oestridae larvae and maggots rely upon their introduction into a host body such as mammalian livestock as Oestridae larvae and maggots cannot survive outside a host body on their own. Known drawbacks for utilizing Oestridae larvae and maggots resident on a host body are the obvious impediments to performing experiments directly upon the Oestridae larvae and maggots while they are attached to a particular host, and the pathological effects that the Oestridae larvae and maggots visit upon the host mammal.

What is needed is a way to cultivate Oestridae larvae and maggots in an in vitro system such that direct experiments can be performed on the Oestridae larvae and maggots without the need for extracting the Oestridae larvae and maggots from a host animal.

SUMMARY

The present subject matter satisfies these needs. In a first embodiment, the present subject matter relates to an in vitro system that cultivates Oestridae larvae and maggots such that direct experiments can be performed on the Oestridae larvae and maggots. The present subject matter accomplishes this by setting up a two-tiered growing apparatus which provides a suitable environment for the cultivation of Oestridae larvae and maggots in an in vitro system. The use of this two-tiered growing apparatus obviates the cumbersome and labor intensive previous method of using host mammals as a breeding environment for Oestridae larvae and maggots and thus addresses the shortcomings of this prior art method of using host mammals.

A second embodiment of the present subject matter further includes selectivity for providing the feeding fluid to the two-tiered growth apparatus.

In an embodiment, the present subject matter relates to a two-tiered in vitro growth apparatus for cultivating Oestridae larvae and maggots, the apparatus comprising: a top tier container; a growth container comprising at least one wall and a floor, both the at least one wall and the floor of the growth container being made of semipermeable material, said growth container also including an interior space for cultivating the Oestridae larvae and maggots; a feeding source for providing a feeding fluid to the growth container for cultivating the Oestridae larvae and maggots. In an embodiment, the present apparatus is capable of providing adequate ventilation, temperature and moisture to the growing maggots. In another embodiment, the bottom of the upper tier is porous to separate the waste fluids coming out from the growing Oestridae larvae and maggots by allowing the dripping of the waste into the bottom tier container.

In an embodiment, the growth container can be any of rectangular, circular, cubical, or any other shape that ensures the larvae are enclosed or surrounded or flanked by the at least one wall that provides the feeding fluid. In one embodiment, the growth container is a rectangular growth container having four walls and a floor, all being made of semipermeable material. In another embodiment, the growth container can be any of a container, box, chamber, enclosure, or the like.

In another embodiment, the present subject matter relates to a method for cultivating Oestridae larvae and maggots, said method comprising: providing a two-tiered in vitro growth apparatus for, the apparatus comprising: a top tier container; a growth container comprising at least one wall and a floor, both the at least one wall and the floor of the growth container being made of semipermeable material, said growth container also including an interior space for cultivating the Oestridae larvae and maggots; a feeding source; and a bottom tier container; placing the Oestridae larvae and maggots inside the growth container; and providing a feeding fluid to the growth container from the feeding source for cultivating the Oestridae larvae and maggots.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF EMBODIMENTS

Figure 1:
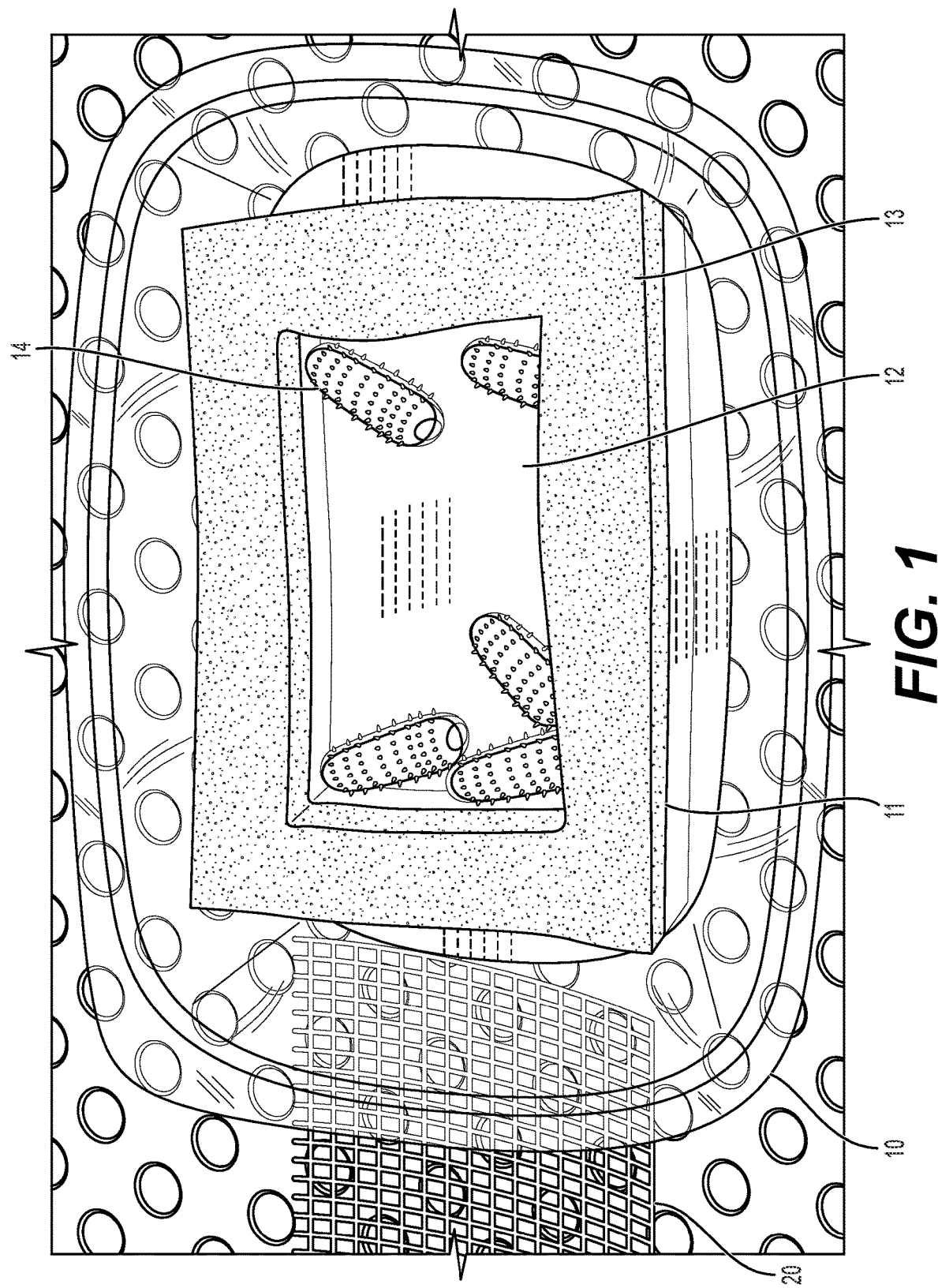
FIG. 1 is a top down view of a first embodiment of the two-tiered growing apparatus.

The following detailed description is merely exemplary in nature and is not intended to limit the described embodiments or the application and uses of the described embodiments. Any implementation described herein with the words "exemplary" or "illustrative" is not necessarily construed as preferred or advantageous over other implementations. All of the implementations described below are exemplary implementations provided to enable persons skilled in the art to make or use the embodiments of the disclosure and are not intended to limit the scope of the disclosure, which is defined by the claims. For the purposes of the description herein, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed therein are not to be considered as limiting, unless the claims expressly state otherwise.

Throughout this application, the term "about" may be used to indicate that a value includes the standard deviation of error for the composition, device or method being employed to determine the value.

As used herein, a "semipermeable material" refers to a material that is one or more of porous, mesh-like, gelatinous, or formed of a matrix. So, any walls or floor of a growth container made of a semipermeable material as described herein are made of a material that is one or more of semipermeable, porous, mesh-like, gelatinous, or formed of a matrix.

The use of the term "or" in the specification and claim(s) is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps. In certain cases, the term "comprising" may be replaced with "consisting essentially of" or "consisting of."

The use of the word "a" or "an" when used herein in conjunction with the term "comprising" in the claims and/or the specification may mean "one," but it is also consistent with the meaning of "one or more," "at least one," and "one or more than one."

In an embodiment, the present subject matter relates to a two-tiered in vitro growth apparatus for cultivating Oestridae larvae and maggots, the apparatus comprising: a top tier container; a growth container comprising at least one wall and a floor, both the at least one wall and the floor of the growth container being made of semipermeable material, said growth container also including an interior space for cultivating the Oestridae larvae and maggots; a feeding source for providing a feeding fluid to the growth container for cultivating the Oestridae larvae and maggots; and a bottom tier container.

In one embodiment, the growth container in the two-tiered in vitro growth apparatus for cultivating Oestridae larvae and maggots rests on a floor of said top tier container and within an interior volume of said top tier container. In another embodiment, the growth container has a mesh overlaid atop the growth container to prevent the Oestridae larvae and maggots from escaping and to let air in for the Oestridae larvae and maggots to breathe.

In an embodiment, the growth container can be any of rectangular, circular, cubical, triangular, or any other shape that ensures the larvae are enclosed or surrounded or flanked by the at least one wall that provides the feeding fluid. In one embodiment, the growth container is a rectangular growth container having four walls and a floor, all being made of semipermeable material. In another embodiment, the growth container can be any of a container, box, chamber, enclosure, or the like.

In an embodiment, said growth container has pores on the at least one wall of the growth container at a level of breathing spiracles of the Oestridae larvae and maggots in the interior space of the growth container through which excess feeding fluid can leak out, and wherein said top and bottom tier containers both are configured to collect excess the feeding fluid and waste from the maggots. In this regard, the top and bottom tier containers are configured to collect the waste fluids from the growing Oestridae larvae and maggots, thereby separating the waste from the growing chamber in order to keep the Oestridae larvae and maggots away from the toxic effects of their waste.

In a different embodiment, said growth container has pores on the floor of the growth container through which excess feeding fluid can leak out, and wherein said top and bottom tier containers both are configured to collect excess feeding fluid and waste from the Oestridae larvae and maggots. In this regard, both the at least one wall and the floor of the growth container can contain the pores.

In further embodiments, the feeding source for providing the feeding fluid has a controller for controlling said providing the feeding fluid at a selected feed rate. In other embodiments, the feeding source can be any source capable of providing the feeding fluid to the growth container in a pulsatile manner. In one non-limiting example in this regard, the feeding source can be a dripper, with the controller for controlling said providing the feeding fluid capable of providing the feeding fluid at a selected drip rate.

In another embodiment, the at least one wall made of semipermeable material absorbs said feeding fluid and provides said feeding fluid to the Oestridae larvae and maggots in the interior space of the growth container.

In a further embodiment, said apparatus is placed inside a ventilated and temperature regulated incubator to ensure a flow of humid air at a controlled temperature is provided to the Oestridae larvae and maggots in the interior space of the growth container.

The first embodiment of the two-tiered in vitro growing apparatus appears as shown in FIG. 1. The two tiered in vitro growing apparatus comprises a top tier comprising a container (10) which provides a foundation and means of support for a growth container (11). According to this embodiment of FIG. 1, the growth container (11) can be rectangular in shape and constructed of a semipermeable material such that it includes four vertical walls and a floor all constructed of the semipermeable material. The growth container (11) can be smaller in volume than the volume of the top tier container (10) and rests on the floor of the interior volume of the top tier container (10). In an alternative embodiment (not shown), the growth container can be configured such that the feeding fluid can be dripped into the center of the growth container and the Oestridae larvae and maggots can feed in a circular pattern around the feeding fluid.

Within the growth container (11) can be an interior space (12) provided explicitly for the cultivation of the Oestridae larvae and maggots (14). The interior space, which is formed by the four semipermeable walls and the floor, contains the Oestridae larvae and maggots (14), and the semipermeable walls keep them appropriately humid and sufficiently fed in a simultaneous fashion. The Oestridae larvae and maggots (14) are provided a feeding fluid from a drip feeder (not shown) by injecting the feeding fluid into, dripping the feeding fluid onto, or pouring the feeding fluid into the semipermeable walls of the growth container (11). This feeding fluid then leaks out into interior space (12) where the resident Oestridae larvae and maggots can feed on it, or they can feed upon the saturated semipermeable walls directly. The floor of the growth container (11), can be porous such that the excess feeding fluid and waste from the Oestridae larvae and maggots can leak downward and away from the interior space, thus ensuring that the Oestridae larvae and maggots won't drown due an over accumulation of the feeding fluid in the interior space (12) of the growth container (11). When the Oestridae larvae and maggots are desired for experiments, they can be efficiently harvested as needed from the interior space (12) of the growth container (11).

Figure 2:
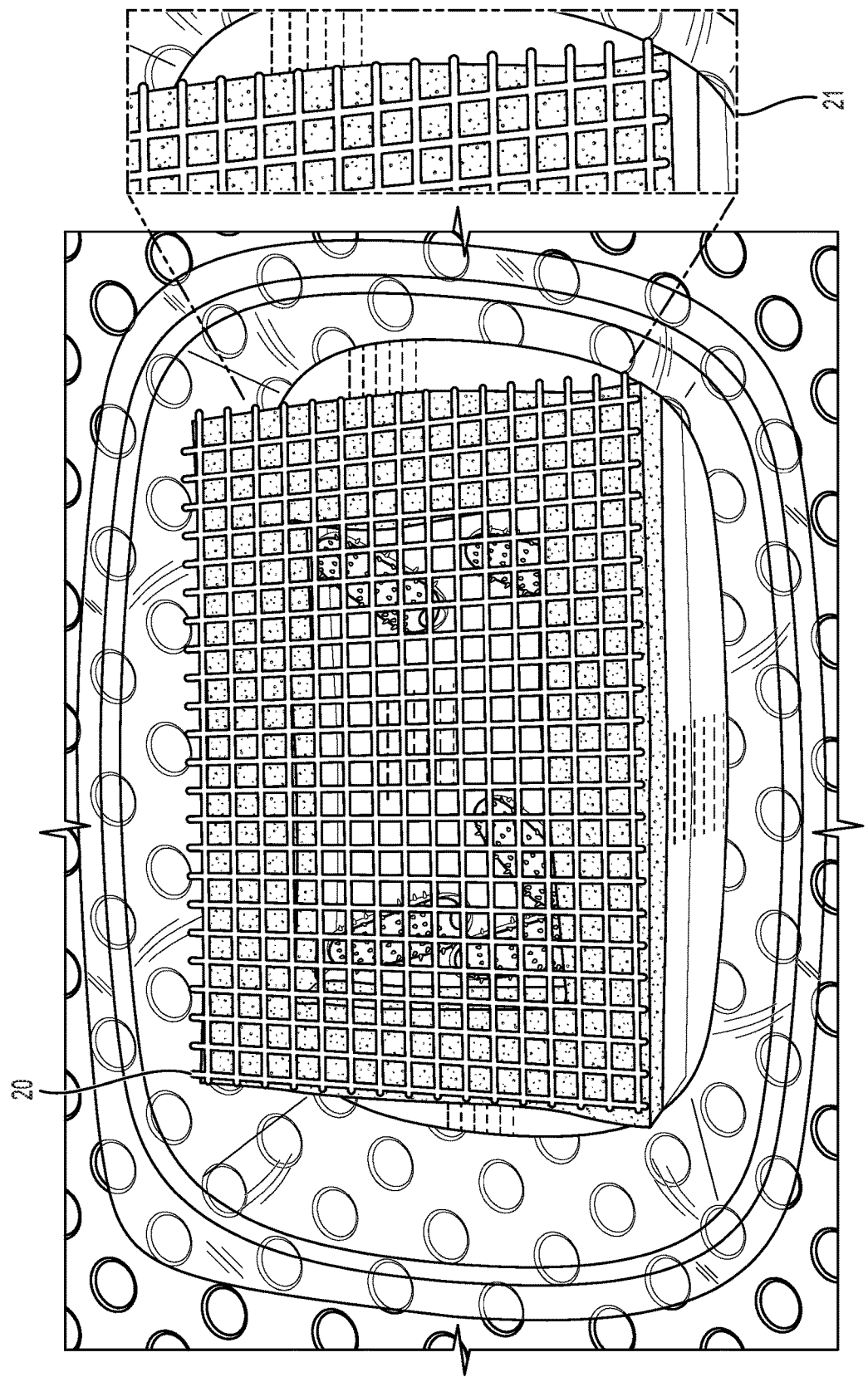
FIG. 2 is a second top down view of the first embodiment of the two-tiered growing apparatus including a mesh for covering the enclosure in which the Oestridae larvae and maggots reside.

FIG. 2 shows a different view of the two-tiered in vitro growth apparatus of the present subject matter. In FIG. 2, a mesh (20) with large pores is overlaid atop the growth container (11) on a top surface (13) of the semipermeable walls to let air in for the Oestridae larvae and maggots (14) and to keep them from escaping. Additionally, safety pores (21) are made on the sides of the growth container (11) at the level of the breathing spiracles of the Oestridae larvae and maggots in order to facilitate the draining of excess feeding fluid such that the Oestridae larvae and maggots (14) do not drown in the growth container (11).

Figure 3:
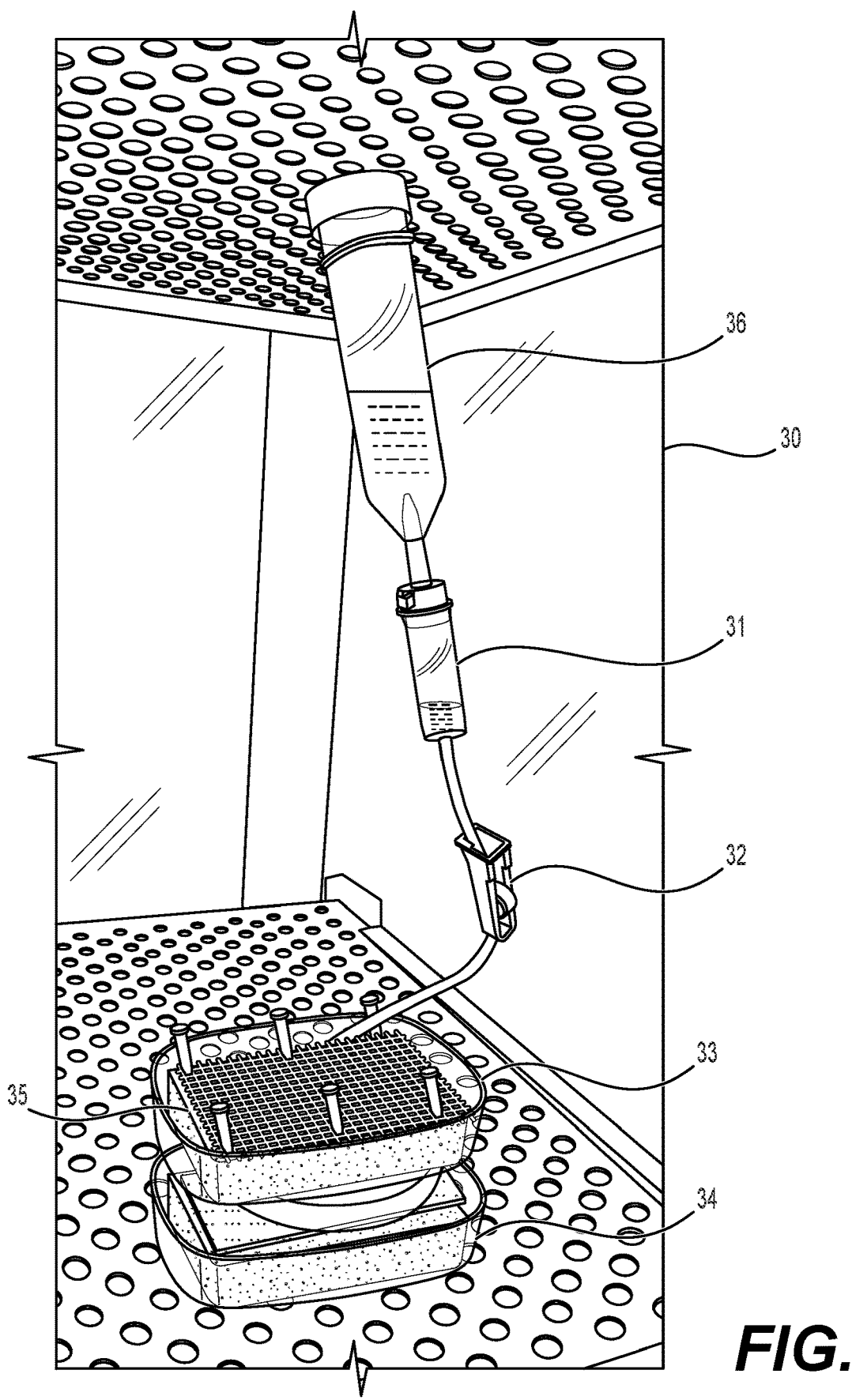
FIG. 3 is a diagram of a second embodiment of the two-tiered growing apparatus as set up within a ventilated incubator.

FIG. 3 shows the two-tiered in vitro growing apparatus as set up within a ventilated incubator (30) which can be maintained at a the requested temperature depending on the scope of the experiment, to provide the desired humidity in the growing environment for the Oestridae larvae and maggots (14). As in FIGS. 1-2, the two-tiered growth apparatus of FIG. 3 also includes a top tier container (33) containing a growth container (35) which is covered by a mesh. This top tier container (33) rests upon a bottom tier container (34) such that the bottom tier container, in an embodiment, is solely responsible for collecting the excess feeding fluid and the waste from the Oestridae larvae and maggots.

In the embodiment of FIGS. 1-2, the top tier container could also exhibit some capabilities for collecting excess feeding fluid and waste from the Oestridae larvae and maggots. That is, both the top tier and the bottom tier can collect excess feeding fluid and the waste from the Oestridae larvae and maggots. Unless otherwise stated, the two-tiered growing apparatus of FIG. 3 performs in the same manner as the two-tiered growing apparatus of FIG. 1. However, a key distinction is that the two-tiered growing apparatus of FIG. 3 also discloses a dripper (31) with a controller (32) to provide a selectable drip rate such that an optimal amount of feeding fluid from the feeding fluid source (36) is provided to the growth container (35) of the top-tier container (33).

In another embodiment, the present subject matter relates to a method for cultivating Oestridae larvae and maggots, said method comprising: providing a two-tiered in vitro growth apparatus for, the apparatus comprising: a top tier container; a growth container comprising at least one wall and a floor, both the at least one wall and the floor of the growth container being made of semipermeable material, said growth container also including an interior space for cultivating the Oestridae larvae and maggots; a feeding source; and a bottom tier container; placing the Oestridae larvae and maggots inside the growth container; and providing a feeding fluid to the growth container from the feeding source for cultivating the Oestridae larvae and maggots.

In an embodiment of the present methods, said growth container rests on a floor of said top tier container and within an interior volume of said top tier container. In another embodiment, the present methods further comprise laying a mesh over said growth container to prevent the Oestridae larvae and maggots from escaping and to let air in for the Oestridae larvae and maggots to breathe.

In an embodiment, the growth container used in the present methods can be any of rectangular, circular, cubical, or any other shape that ensures the larvae are enclosed or surrounded or flanked by the at least one wall that provides the feeding fluid. In one embodiment, the growth container is a rectangular growth container having four walls and a floor, all being made of semipermeable material. In another embodiment, the growth container can be any of a container, box, chamber, enclosure, or the like.

In a further embodiment, said feeding source for providing the feeding fluid has a controller for controlling said providing the feeding fluid at a selected feed rate. In this regard, said providing the feeding fluid comprises injecting, dripping, or pouring the feeding fluid into the at least one wall made of semipermeable material. The at least one wall made of semipermeable material can absorb said feeding fluid and provide said feeding fluid to the Oestridae larvae and maggots in the interior space of the growth container.

In other embodiments, the feeding source can be any source capable of providing the feeding fluid to the growth container in a pulsatile manner. In one non-limiting example in this regard, the feeding source can be a dripper, with the controller for controlling said providing the feeding fluid capable of providing the feeding fluid at a selected drip rate.

In certain aspects of the present methods, the providing the feeding fluid to the Oestridae larvae and maggots in the interior space of the growth container comprises leaking the feeding fluid from the at least one wall made of semipermeable material into the interior space of the growth container. In further and/or additional aspects of the present methods, the Oestridae larvae and maggots in the interior space of the growth container suck the feeding fluid from the four walls of semipermeable material that have absorbed said feeding fluid. In other aspects of the present methods, the feeding fluid can be dripped in the semipermeable membrane, and the Oestridae larvae and maggots can suckle on the walls of the semipermeable membrane, similar to their nature inside mammalian hosts.

In an embodiment, the present methods further comprise collecting excess feeding fluid and waste from the Oestridae larvae and maggots through pores on the at least one wall of the growth container at a level of breathing spiracles of the Oestridae larvae and maggots in the interior space of the growth container, and/or through pores on the floor of the growth container at a level of breathing spiracles of the Oestridae larvae and maggots in the interior space of the growth container.

In a further embodiment, the present methods further comprise placing the apparatus inside a ventilated incubator to ensure a flow of humid air at a controlled temperature is constantly provided to the Oestridae larvae and maggots in the interior space of the growth container. In this regard, the ventilated incubator can be maintained at a constant temperature of about 30° C. to about 40° C., or at about 37° C., to provide the desired humidity in the growing environment for the Oestridae larvae and maggots.

It is to be understood that the method and system for cultivating larvae or maggots of the Oestridae family is not limited to the specific embodiment described above but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A two-tiered in vitro growth apparatus for cultivating Oestridae larvae and maggots, the apparatus comprising:
a top tier container;
a growth container comprising at least one wall and a floor, both the at least one wall and the floor of the growth container being made of semipermeable material, said growth container also including an interior space for cultivating the Oestridae larvae and maggots;

a feeding source for providing a feeding fluid to the growth container for cultivating the Oestridae larvae and maggots; and a bottom tier container.

2. The two-tiered in vitro growth apparatus for cultivating Oestridae larvae and maggots as recited in claim 1, wherein said growth container rests on a floor of said top tier container and within an interior volume of said top tier container.

3. The two-tiered in vitro growth apparatus for cultivating Oestridae larvae and maggots as recited in claim 2, wherein said growth container has a mesh overlaid atop the growth container to prevent the Oestridae larvae and maggots from escaping and to let air in for the Oestridae larvae and maggots to breathe.

4. The two-tiered in vitro growth apparatus for cultivating Oestridae larvae and maggots as recited in claim 2, wherein said feeding source for providing the feeding fluid has a controller for controlling said providing the feeding fluid at a selected feed rate.

5. The two-tiered in vitro growth apparatus for cultivating Oestridae larvae and maggots as recited in claim 4, wherein said at least one wall made of semipermeable material absorbs said feeding fluid and provides said feeding fluid to the Oestridae larvae and maggots in the interior space of the growth container.

6. The two-tiered in vitro growth apparatus for cultivating Oestridae larvae and maggots as recited in claim 2, wherein said growth container has pores on the at least one wall of the growth container at a level of breathing spiracles of the Oestridae larvae and maggots in the interior space of the growth container through which excess feeding fluid can leak out, and wherein said top and bottom tier containers both are configured to collect the excess feeding fluid and waste from the Oestridae larvae and maggots.

7. The two-tiered in vitro growth apparatus for cultivating Oestridae larvae and maggots as recited in claim 2, wherein said growth container has pores on the floor of the growth container through which excess feeding fluid can leak out, and wherein said top and bottom tier containers both are configured to collect excess feeding fluid and waste from the Oestridae larvae and maggots.

8. The two-tiered in vitro growth apparatus for cultivating Oestridae larvae and maggots as recited in claim 1, wherein said apparatus is placed inside a ventilated incubator.

9. A method for cultivating Oestridae larvae and maggots, said method comprising:

providing a two-tiered in vitro growth apparatus for, the apparatus comprising:

a top tier container;

a growth container comprising at least one wall and a floor, both the at least one wall and the floor of the growth container being made of semipermeable material, said growth container also including an interior space for cultivating the Oestridae larvae and maggots;

a feeding source; and a bottom tier container;

placing the Oestridae larvae and maggots inside the growth container; and providing a feeding fluid to the growth container from the feeding source for cultivating the Oestridae larvae and maggots.

10. The method as recited in claim 9, wherein said growth container rests on a floor of said top tier container and within an interior volume of said top tier container.

11. The method as recited in claim 10, further comprising laying a mesh over said growth container to prevent the Oestridae larvae and maggots from escaping and to let air in for the Oestridae larvae and maggots to breathe.

12. The method as recited in claim 10, wherein said feeding source for providing the feeding fluid has a controller for controlling said providing the feeding fluid at a selected feed rate.

13. The method as recited in claim 12, wherein said providing the feeding fluid comprises injecting, dripping, or pouring the feeding fluid into the at least one wall made of semipermeable material.

14. The method as recited in claim 13, wherein said at least one wall made of semipermeable material absorbs said feeding fluid and provides said feeding fluid to the Oestridae larvae and maggots in the interior space of the growth container.

15. The method as recited in claim 14, wherein the providing the feeding fluid to the Oestridae larvae and maggots in the interior space of the growth container comprises leaking the feeding fluid from the four walls made of semipermeable material into the interior space of the growth container.

16. The method as recited in claim 14, wherein the Oestridae larvae and maggots in the interior space of the growth container suck the feeding fluid from the at least one wall of semipermeable material that have absorbed said feeding fluid.

17. The method as recited in claim 10, further comprising collecting excess feeding fluid and waste from the Oestridae larvae and maggots through pores on the at least one wall of the growth container at a level of breathing spiracles of the Oestridae larvae and maggots in the interior space of the growth container.

18. The method as recited in claim 10, further comprising collecting excess feeding fluid and waste from the Oestridae larvae and maggots through pores on the floor of the growth container at a level of breathing spiracles of the Oestridae larvae and maggots in the interior space of the growth container.

19. The method as recited in claim 10, further comprising placing the apparatus inside a ventilated incubator to ensure a flow of humid air at a controlled temperature is constantly provided to the Oestridae larvae and maggots in the interior space of the rectangular growth container.

\* \* \* \* \*